United States Patent [19]

Blomet et al.

[11] Patent Number: 5,763,486
[45] Date of Patent: Jun. 9, 1998

[54] PROCESS FOR PREPARING A COMPOSITION FOR THE TREATMENT OF THERMAL OR CHEMICAL BURNS

[75] Inventors: Joël Blomet, Valmondois;
Marie-Claude Blomet épouse Meyer, 243 Rue de Vaugirard, Paris 75015;
Dominique Friard épouse Jahan, Maurecourt, all of France

[73] Assignee: Marie-Claude Blomet Epouse Meyer, Paris, France

[21] Appl. No.: 730,645

[22] Filed: Oct. 11, 1996

Related U.S. Application Data

[62] Division of Ser. No. 227,648, Apr. 14, 1994, Pat. No. 5,587,400.

[30] Foreign Application Priority Data

Apr. 19, 1993 [FR] France ................ 93 04585
Jul. 6, 1993 [FR] France ................ 93 08278

[51] Int. Cl.[6] ................ A01N 37/12; A01N 61/00; A61K 38/28; A61K 38/16
[52] U.S. Cl. ................ 514/566; 514/1; 514/4; 514/6; 514/191
[58] Field of Search ................ 514/566, 191, 514/1, 4, 6

[56] References Cited

FOREIGN PATENT DOCUMENTS 2 604 900  10/1986  France ................ A61K 7/40
3-188149(AB)  8/1991  Japan.

OTHER PUBLICATIONS

Abstract of JP 3 188 149 (Otsuka Seiyaku Kojy).
Guy & Seabright et al, *Chemical Abstracts*, vol. 113, No. 7 abstract 53932p, 1990, p. 204.
Guy & Jones et al, *Chemical Abstracts*, vol. 114, No. 21, abstract 204958a, 1991, p. 610.

*Primary Examiner*—Lynette F. Smith
*Assistant Examiner*—Brett Nelson
*Attorney, Agent, or Firm*—Larson & Taylor

[57] ABSTRACT

The object of the present invention is a physiological composition for the treatment of thermal and chemical burns comprising an efficient amount of Al(OH)Y complex formed between the aluminum ion $Al^{3+}$ and an ethylenediaminetetraacetic ligand (ligand Y).

14 Claims, No Drawings

PROCESS FOR PREPARING A COMPOSITION FOR THE TREATMENT OF THERMAL OR CHEMICAL BURNS

This is a division of application Ser. No. 08/227,648 filed Apr. 14, 1994, now U.S. Pat. No. 5,587,400.

The object of the invention relates to a physiological composition intended for treating thermal or chemical burns.

It also relates to the process of preparing this composition, a useful concentrate for its preparation as well as the application of said composition in the treatment of internal or external burns.

When handling corrosive and irritating products, for example, strong acids or strong bases, in particular in factories and laboratories, it frequently happens that accidental projections or splashes of these products come into contact with the skin, hair or eyes. It may even happen that these products be ingested by accident.

Also, it unfortunately quite often happens that reactive, corrosive or irritating chemicals, used, for example, during "do-it-yourself", or odd jobs or gardening, result in serious domestic accidents, these accidents being all the more regrettable and unfortunate as they most frequently involve young children. The products or chemicals in question may, for example, include strong acids and strong bases, scouring or pickling agents, washing liquids and powders, detergents, solvents, fertilizers, insecticides, fungicides and weed killers. These chemicals or products may accidentally contact an external part of the body or even be ingested.

In the event of such accidents, it is of the highest importance to be able to act rapidly in order to prevent, or at least restrict as far as possible, the occurrence of burns with irreversible consequences.

It is obviously of common practice to rinse the injured part of the body with water without any additive, for example with tap water. However, this simple method, easily applicable and accessible, and which may give relatively satisfactory results on the least fragile parts of the body, such as the hands, most of the time turns out to be insufficient when the eye must be treated, and this method is obviously thoroughly inefficient when such corrosive products have been ingested.

Studies have demonstrated that the neutralization of a strong acid or strong base by water requires several hours, which means, that in the case of an eye injury, for example, the corrosive or irritating agent continues its aggressive action on the endothelial cells, which may lead to disastrous and irreversible effects.

Furthermore, it should also be stressed that the effects of this slow action are aggravated since water is hypotonic in relation to the skin or to the eye. Thus, in the case of the eye, the water osmotically penetrates the stroma, simultaneously carrying along part of the aggressive agent resulting in edema and lesions in the endothelial cells.

In order to remedy these noxious effects, it has been suggested to "wash" the aggressive agents involved by means of solutions containing a reactive product with a contrary effect. Thus, it has been proposed to wash the acids with a solution of a weak base compound and to wash the bases with a solution of a weak acid compound, these solutions being preferably isotonic with the part of the body to be treated, for example the lachrymal liquid in the case of the eye.

Such solutions are thus available on the market, for example, solutions based on boric acid to wash the burns by means of the bases and based on sodium bicarbonate to wash the burns by means of the acids.

Such solutions generally provide satisfactory results when the agent responsible for the burn is known. Unfortunately, this is often not the case in the common practice encountered in the industry or laboratory, not to mention the case of domestic accidents.

It is therefore desirable to be able to resort to a useful and efficient solution, regardless of the type of aggressive agent.

To this end, there has already been proposed buffers, that is solutions comprising two ionic forms derived from a same ion such as for example phosphate ion, converting themselves one into the other by acid-base reaction. There is thus available on the market a solution comprising two ions derived from phosphate ion $PO_4^{3-}$, i.e. $HPO_4^{2-}$ and $H_2PO_4^-$ ions.

In fact, since the solutions of this type do not totally offer the expected efficiency, especially on account of the distribution of the equilibrium constants of the occurring reactions, much better solutions have been searched, proposed and adopted. Thus, the French Patent 86 11 754 discloses a single physiological solution providing a satisfactory efficiency and rapid action both against acids and bases, by using in the formulation of this solution, one or several ampholytes selected in such a way that the acid pK on one hand, and the basic pK on the other hand, of the resulting solution yields certain predetermined values. It should be reminded that an ampholyte is an electrolyte comprising both the acid function and the basic function and therefore, providing at least two dissociation constants, one corresponding to the acid function, the other to the basic function.

Thus, the aforesaid patent disclosed a physiological aqueous solution for washing the parts of a human or animal body contacted by an isotonic or slightly hypertonic acid or base, characterized in that it includes, as active agent(s), one or several ampholytes selected in such a way that:

the pH of the solution is in the range of 6 to 8, the smallest of the acid pK is in the range of 6 to 10 and the highest of the basic pK is in the range of 5 to 8, and the highest basic pK is lower than the smallest acid pK.

Still according to the aforesaid patent, the preferred ampholytes are histidine dihydrochloride and histidylhistidine trihydrochloride, most preferably histidine dihydrochloride.

Unfortunately, this product is very costly and therefore dramatically restricts the scope of use of the physiological aqueous solutions containing same, this range of use being heretofore reserved to the practice in industrial sites and laboratories.

Besides, it is to be regretted that this product normally provides a relatively reduced scope of utilization as compared with the corrosive and irritating products likely to be encountered. It would therefore be of interest to be able to resort to a physiological aqueous solution containing a product providing a wider spectrum of activity against corrosive and irritating agents. In this respect, it should be noticed that the efficiency of such product must not be simply interpreted or evaluated in terms of acid-base neutralizing reaction, but that it must principally be evaluated as a function of its capacity to restore, in the most efficient and rapid possible way, the normal physiological conditions prevailing before the occurrence of the aggression caused by the corrosive and irritating agents contacted or ingested by accident. Thus, we are at present searching for a solution which is efficient not only against strong acids and/or strong bases but also against other corrosive or irritating products.

Besides the products proposed and used according to the prior art, such as histidine dihydrochloride provide a limited efficiency, this limitation being essentially due to the fact that the concentration of active product in the solution cannot exceed certain values, such values being governed by osmotic pressures. It can easily be understood that physiological solutions with excessively high osmotic pressures cannot be applied to some part or other of the body, which in practice limits the possibility of increasing the concentrations of active products in physiological aqueous solutions.

There would therefore be an obvious interest in being able to resort to an ampholyte product which does not prove too costly, and which provides a wide spectrum of use against corrosive and irritating products, and which may provide a notably higher efficiency than those already known with an equivalent osmotic pressure.

Now, the merit of the Applicant is to have found and developed such a product and the object of the invention is therefore a physiological composition for the treatment of thermal or chemical burns, this composition being characterized in that it includes an efficient amount of at least a complex formed between the aluminum ion $Al^{3+}$ and the ethylenediamine-tetraacetic ligand (EDTA) of the formula $(CH_2 COO^-)_2 N—CH_2—CH_2—N(CH_2COO^-)_2$.

Y designates the EDTA ligand, four complexes can be formed, according to the formula:

AlY, AlHY, Al(OH)Y or Al(OH)$_2$Y

The physiological composition according to the invention therefore comprises an efficient amount of at least one of these complexes and, preferably, contains an efficient amount of the complex Al(OH)Y, this complex proving to be the most efficient as ampholyte usable in the intended application of the present invention.

Most generally, the physiological composition according to the invention comprises a concentration of said complexes of 0.05 mole/l to 1.5 mole/l, preferably from 0.1 mole/l to 1.0 mole/l and still most preferably from 0.1 mole/l to 0.4 mole/l.

According to a particularly advantageous embodiment, the composition according to the invention, comprises a concentration of complex Al(OH)Y from 0.05 mole/l to 1.0 mole/l and preferably from 0.1 mole/l to 0.6 mole/l and still most preferably from 0.1 mole/l to 0.4 mole/l.

Naturally, said complexes are, as the case may be, associated with cations, in particular $Na^+$.

Other ampholytes may also, although this may not necessarily be indispensable, be present in the composition according to the invention. These ampholytes may include disodic citrate, alanine, disodic glutamate, glycocoll, lysine, alanyl-alanine, sodium bicarbonate, trisodic salt of EDTA.

The composition according to the invention may also contain other products commonly used in this type of compositions such as sodium chloride and sugars, in particular, glucose whose concentration is selected in such a way to adjust the isotonicity or hypertonicity of the composition to a given value according to the applications or the parts of the body involved.

The physiological composition may also contain glycerol, glycols, solvents, in particular alcohols, possibly present in order to facilitate the solubilization of other components contained in the constitution of said composition.

It may besides contain dyeing agents, flavoring agents, tasting agents, protecting agents or preservatives.

The protecting agents or preservatives are used within the limits authorized by the regulations, these preservatives being advantageously in the form of a solution in propyleneglycol. The preservative may include for example diazolidinylurea, methylparaben or propylparaben. These compounds are generally comprised between 0.01% and 0.5% of the total weight of the composition.

The Applicants' Company has found that the gelification of the composition based on said complexes makes it possible to obtain various advantages, certain of them not being predictable a priori such as for example the reduction of keloid scars, the very important reduction of edemas and substantial acceleration in the wound healing, and to provide medical emergency units as well as private individuals with a product which is very simple to use, versatile and extremely efficient.

In the scope of the present invention, the term "gel" or gelification means an aqueous composition which provides a sufficient viscosity able to remain for a sufficient time period on the skin or on the burned organs. This viscosity is generally superior to 1000 centipoises and most generally comprised between 2000 and 100 000 cps, preferably between 5 000 and 50 000 cps.

The presentation in the form of a gel of the composition for the internal or external treatment of thermal or chemical burns makes it possible to combine the good thermodynamic properties (heat capacity, thermo conductivity) and interesting osmotic properties.

An obvious interest, both in the treatment of a thermal burn and of a chemical burn consists in fact in having a higher osmotic pressure, however, without being noxious. The osmotic pressure of the composition according to the invention, in the form of a gel, is from 900 to 1100 mosmoles/kg. This high osmotic pressure makes it possible in the case of chemical burns, to perform a pumping of the dangerous product and, in the case of a thermal burn, to resorb the edema, thereby resulting in a better nutrition of the superficial layers.

The gel form, or more generally this viscous presentation, is obtained by incorporating in the composition according to the invention at least one thickener of a nutritional quality. The thickeners in question may for example be xanthane gums, guar gums, carouba gums, native or modified starches, carraghenates, tragacanth gum, arabic gum, pectines, cellulose ethers, in which in particular carboxymethylcellulose, agar-agar, alginates.

These thickeners may be used alone or in combination. Preferably, according to the invention, xanthane gum, as the case may be associated with guar gum or with carouba gum.

The amount of thickener contained in the composition according to the invention is generally comprised between 0.25 and 3, preferably between 0.5 and 2.5, and most preferably still between 0.75 and 2.25 weight % related to the total weight of the composition.

The composition in the form of a gel according to the invention, also contains, advantageously, glycerol to facilitate the dispersion of the thickener. Glycerol is generally present in an amount from 0.25 to 5, preferably from 0.5 to 4 and still most preferably from 0.5 to 3 weight % related to the total weight of the composition.

Preferably, it also contains an essential oil, advantageously constituted by tea tree oil (melalenca alternifolia), whose remarkable properties as germicides, bactericides and fungicides are well known. The concentration of essential oil in the composition may be established between 0.10 and 2, preferably between 0.15 and 1.5 and most preferably still between 0.2 and 1 weight % related to the total weight of the composition.

A surfactant, or wetting agent may be added to the composition in the form of a gel according to the invention. During the manufacture of the gel, this surfactant facilitates the dispersion of the thickener, and in the final product, it contributes to the adhesion of the gel to the skin and to the clothes of the burned person. This surfactant is generally added in an amount comprised between 0.010 and 0.75, and preferably between 0.050 and 0.50 weight % related to the total weight of the composition. It is advantageously constituted by octoxynol or capryl caprilyl caprilyl glucoside.

The composition in the form of a gel according to the invention comprising at least a thickener of a nutritional quality and, advantageously, glycerol, an essential oil as well as a surfactant is preferably contained in a pressurized container in order to facilitate its application.

The composition in the form of a gel according to the invention, makes it possible to obtain a much better efficiency than the solution for the treatment of thermal or chemical burns of the prior art and also makes it possible for emergency medical units, as well as for particularly individuals, as the case may be, to resort to a single product, irrespective of the type of burn.

Preferably, the composition in the form of a gel according to the invention is contained in a pressurized container, facilitating its application.

The composition according to the invention advantageously provides a pH comprised between 6 and 9.

In this respect, it should be pointed out that advantageously, the pH can be stabilized by means of boric acid and/or glycocoll. Boric acid and glycocoll besides yield the advantage of strengthening the antibase action.

The composition according to the invention, thanks to its amphoteric and chelating character, halts the progression of the chemicals splashed or ingested by accident, but also makes it possible to reduce the acidose resulting from thermal burns.

The object of the invention is also a process for the manufacture of the physiological composition according to the invention, this process being characterized by the fact that metal aluminum is oxidized in a strong alkaline solution, preferably a soda, the aluminum ion is complexed in a basic solution thus obtained by acid EDTA, the solution obtained is then brought to the required concentration with the possible introduction of additives, buffers and solvents, as required.

Aluminum, although being a highly reducing metal ($E_o = -1.66$ V) in aqueous solutions, covers itself with an oxide protecting film between pH 5 and 11. When aluminum is subjected to the action of alkaline solutions, the oxide layer dissolves and aluminates of the formula $Na[Al(OH)_4]$ are formed.

The exposed aluminum equally reacts by forming aluminates.

The global equation describing the process of the solution of aluminum in an aqueous alkaline solution is therefore as follows:

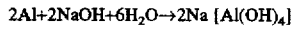

The complexing reaction of acid EDTA is then carried out on the alkaline solution of aluminates thus obtained. This complexing reaction is relatively difficult to achieve since aluminum usually complexes with tetrasodic EDTA. In the present case, the dissolution of acid EDTA and complexing with aluminum ion must be performed in the same operation.

In order that this complexing operation be optimally performed, the acid EDTA is preferably added rapidly and in a single operation to the solution of aluminates, at a high temperature, preferably close to the boiling temperature, and under stirring.

If EDTA is added little by little, the aluminum ion can be found in excess during the reaction and hydroxide is formed. Equally, if the reaction is carried out at a low temperature, EDTA does not properly dissolve and a deposit then builds up at the bottom of the reaction vessel. In both cases, the yields of formation of the sought complexes are thus less satisfactory.

The equation for the formation of the preferred complex can be globally written as follows (Y always designates the EDTA ligand):

Preferably, the reaction temperature at the time the acid EDTA is added is higher than 70° C. and preferably higher than approximately 85° C.

The reaction product obtained upon completion of the reaction includes AlY, AlYH, AlYOH, $AL(OH)_2Y$ complexes and essentially the preferably desired AlYOH complex.

This reaction product may be sold such as it is, possibly following evaporation or powder forming, for example by spray atomizing and then builds up an aqueous concentrate or a powdered concentrate, usable for the preparation of final physiological solutions.

These solutions are prepared by diluting said concentrates with physiological saline water up to the concentration in the desired active complexes, with, as the case may be, the addition of other ampholytes, buffers or pH rectifiers, preservatives, dyes, co-solvents or other additives. This solution is then sterilized. When the composition according to the invention is presented under the form of a gel, there is added under stirring to a solution comprising at least AlY, AlHY, Al(OH)Y or $Al(OH)_2Y$ complex a sufficient amount of at least one nutritional thickener, such as those previously described, as well as if required, glycerol, an essential oil, preferably constituted by tea tree oil or a surfactant; then, the composition thus obtained is conditioned, preferably in a pressurized packing and is subsequently sterilized.

Preferably, the preparation of said composition takes place in a sterilized room.

The composition according to the invention may be used for external use, for cooling the thermal burns, for stopping and washing the chemical burns or for reducing the edemas and protecting the burns. It may also be used for internal use in the case, for example, of chemical gastric burns, in order to stop the progression of the chemical product and perform an esophageal dressing.

Examples of compositions according to the invention are given hereafter as illustration.

EXAMPLE 1

Preparation of a Concentrate of Complexes According to the Invention

In a reaction vessel equipped with a gas extractor, there is introduced the required amount of water, subsequently the required amount of soda in tablets is dissolved prior to adding aluminum. When the aluminum is dissolved, the vessel is heated to a temperature of 90° C. and acid EDTA is added in one time by strongly stirring up to dissolution of the product.

The quantities used in grams per liter are as follows:

soda: 28 g/l
aluminum: 8.5 g/l
acid EDTA: 94 g/l

The concentrate thus obtained may be used for the preparation of a physiological solution according to the invention.

EXAMPLE 2

A physiological aqueous solution is thus prepared from said concentrate, this aqueous solution comprising:

disodic salt of AlOHY (molecular weight of 378.20): 98.3 g/l, that is 0.26 mole/l, monosodic salt of AlY (molecular weight of 418.20): 25 g/l, that is 0.6 mole/l, orthoboric acid (molecular weight of 61.8): 21 g/l, that is 0.34 mole/l, sodium chloride (molecular weight of 58.44): 12.8 g/l, that is 0.22 mole/l, demineralized water, qs: 1 liter

EXAMPLE 3

Another aqueous solution according to the invention is prepared with the following composition:

disodic salt of AlYOH ion: 35.3 g, glycocoll: 7.0 g, sodium chloride: 16.3 g, sodic methyl hydroxy-4 benzoate: 0.5 g, demineralized water, qs: 1000 ml

EXAMPLE 4

Another physiological aqueous solution in accordance with the invention has the following composition:

disodic salt of AlYOH: 106.0 g, glycocoll: 21.0 g, sodium chloride: 12.8 g, sodic methyl hydroxy-4 benzoate: 0.5 g, demineralized water, qs: 1000 ml.

In accordance with the law in force concerning cosmetics and sanitary body products, innocuity tests were performed on the products, in particular on the composition of example 2 and the results are as follows:

the product is considered as non irritating when applied to the skin of a rabbit; the index of primary skin irritation is thus 0.5.

the product is considered as non irritating when applied to the eye of a rabbit.

No eye reaction was observed on the animals, the index of eye irritation is 0.0.

the LD 0 of the product orally administered to the rat is higher or equal to 5000 mg/kg, dose at which no sign of toxicity was observed.

EXAMPLE 5

Composition for External Use the formulation is as follows:

| | |
|---|---|
| ampholyte complex: ethylenediamine acid tetraacetic, disodic salt (disodic salt of Al(OH)Y, a molecular weight of 378.20) | 3.60 g |
| orthoboric acid | 0.55 g |
| sodium chloride | 1.60 g |
| xanthane gum, trade mark KELTROL available from KELCO company | 1.25 g |
| glycerol | 1.00 g |
| non-ionic surfactant, trade mark TRITON CG-110, sold by UNION CARBIDE | 0.10 g |
| Germaben II | 1.00 g |

-continued

| | | |
|---|---|---|
| propylenglycol: 56% | | |
| diazolidinylurea: 30% | | |
| methylparaben: 11% | | |
| propylparaben: 3% | | |
| tea tree essential oil | | 0.50 g |
| demineralized water, qs | | 100 ml |

EXAMPLE 6

Formulation for Internal Use

The formulation comprises the following products:

| | |
|---|---|
| ampholyte complex: | |
| ethylenediaminetetraacetic acid, disodic salt, complex of hydroxide aluminum (disodic salt of Al(OH)Y molecular weight 378.20) | 9.60 g |
| ethylenediaminetetraacetic, trisodic salt, aluminum complex (trisodic salt of Al(OH)$_2$Y, molecular weight 418.20) | 2.45 g |
| orthoboric acid | 2.05 g |
| xanthane gum, trade mark KELTROL, sold by KELCO company | 1.25 g |
| glycerol | 1.00 g |
| non-ionic surfactant, trade mark TRITON CG-110, sold by UNION CARBIDE company | 0.10 g |
| demineralized water, qs | 100 ml |

The osmotic pressure of said compositions ranges between 900 and 1100 mosmoles/kg. It is therefore higher than the osmotic pressure of a corresponding solution comprising the same ampholyte complexes, this osmotic pressure being then about 850 mosmoles/kg. It is besides much higher than the osmotic pressure of a solution of 9% of sodium chloride, this osmotic pressure being established close to 290 mosmoles/kg.

The two formulations above have been evaluated as far as their toxicity is concerned.

They are considered as non irritating for the skin following the results of a skin irritation test on the rabbit.

They are also non irritating to the eyes following the results of an eye irritation test to the rabbit.

The LD 50 on the intact skin of the rat is higher than 2000 mg/kg, and the composition is therefore considered as non toxic for the skin.

The oral LD 50 on the rat is higher than 2000 mg/kg, dose at which no sign of toxicity could be observed.

The above data demonstrate the perfect harmlessness of the composition according to the invention.

The invention therefore provides an efficient, versatile composition, simple in use and with a perfect harmlessness for the internal or external treatment of chemical or thermal burns.

What is claimed is:

1. Process for the preparation of a physiological composition for the treatment of thermal or chemical burns, comprising the steps of:

oxidizing aluminum metal in an aqueous alkaline solution to form a basic solution of aluminates, adding acid EDTA to said basic solution to form a complex of the formula Al(OH)Y where Y is the ethylenediaminetetracetic ligand, recovering the solution containing said complex.

2. Process for the preparation of a physiological composition according to claim 1 wherein the acid EDTA is added at a temperature of 70° C. to 90° C.

3. Process for the preparation of a physiological composition according to claim 2, wherein the acid EDTA is added at a temperature of 85° C. to 90° C.

4. Process for the preparation of a physiological composition according to claim 1, wherein the complex is present in the solution at a concentration of between 0.05 mole/l and 1.5 mole/l.

5. Process for the preparation of a physiological composition according to claim 1, wherein the complex is an Al(OH)Y complex and its concentration in the solution is between 0.05 mole/l and 1.0 mole/l.

6. Process for the preparation of a physiological composition according to claim 1, wherein the aqueous alkaline solution is a solution of sodium hydroxide.

7. Process for the preparation of a physiological composition according to claim 1, wherein the solution containing the complex has a pH of between 6 and 9.

8. Process for the preparation of a physiological composition according to claim 1, wherein at least one thickener is added to the solution containing the complex to form a gel.

9. Process for the preparation of a physiological composition according to claim 8, wherein the thickeners are selected from the group consisting of xanthane gums, guar gums, carouba gums, native starches, carraghenates, tragacanth gum, arabic gum, pectins, cellulose ethers, carboxymethyl cellulose, agar-agar and alginates.

10. Process for the preparation of a physiological composition according to claim 9, wherein the thickeners are added to the physiological composition in an amount from 0.25 to 3% by weight related to the total weight of the composition.

11. Process for the preparation of a physiological composition according to claim 9, wherein glycerol is added to the physiological composition in a amount from 0.25 to 5% by weight related to the total weight of the composition.

12. Process for the preparation of a physiological composition according to claim 9, wherein a germicide, bactericide or fungicide is added to the physiological composition in an amount comprised between 0.10 and 2% by weight related to the total weight of the composition.

13. Process for the preparation of a physiological composition according to claim 9, wherein a surfactant or wetting agent is added to the physiological composition in an amount comprised between 0.01 and 0.75% by weight related to the total weight of the composition.

14. Process for the preparation of a physiological composition according to any one of claims 9 to 13, wherein the composition is contained in a pressurized container.

* * * * *